United States Patent [19]
Ellis et al.

[11] 4,268,631
[45] May 19, 1981

[54] APOGLUCOSE OXIDASE PREPARATION

[75] Inventors: Paul B. Ellis, High Wycombe; David L. Morris, Stoke Poges, both of England

[73] Assignee: Miles Laboratories, Inc., Elkhart, Ind.

[21] Appl. No.: 45,191

[22] Filed: Jun. 4, 1979

[51] Int. Cl.³ .............................................. C12N 9/04
[52] U.S. Cl. .................................... 435/190; 435/25; 435/815
[58] Field of Search ......................... 435/190, 815, 25

[56] References Cited
PUBLICATIONS

Yoshimura et al., Journal Biochemistry, (Tokyo), vol. 69, pp. 969–972.
Swoboda, Biochimica et Biophysica Acta, vol. 175, pp. 365–379, (1969).
Zappelli et al., Eur. J. Biochem., vol. 89, pp. 491–499, (1978).

Primary Examiner—Lionel M. Shapiro
Attorney, Agent, or Firm—Andrew L. Klawitter

[57] ABSTRACT

An apoglucose oxidase preparation having a residual glucose oxidase activity of less than 0.05%, and preferably less than 0.005%. The preparation is obtained by incubation of glucose oxidase in aqueous solution at a pH of less than about 2 and in the presence of about 20 to about 40, preferably about 30, percent by volume glycerol, and separating resulting dissociated prosthetic group, flavin adenine dinucleotide, from apoglucose oxidase by column chromatography, preferably on cross-linked dextran gel. The purified apoglucose oxidase is useful as a reagent in specific binding assays employing flavin adenine dinucleotide as a label.

21 Claims, No Drawings

APOGLUCOSE OXIDASE PREPARATION

BACKGROUND OF THE INVENTION

1. FIELD OF THE INVENTION

The enzyme glucose oxidase, which catalyzes the oxidation of glucose in the presence of oxygen to gluconic acid and hydrogen peroxide, is composed of the organic prosthetic group flavin adenine dinucleotide (FAD) conjugated to the protein portion of the enzyme, referred to as the apoenzyme. The protein portion, or apoenzyme, of glucose oxidase is referred to as apoglucose oxidase and is not enzymatically active when separated from FAD. The present invention relates to methods for preparing apoglucose oxidase, that is, for dissociating and separating FAD from the apoenzyme of glucose oxidase.

2. DESCRIPTION OF THE PRIOR ART

Apoglucose oxidase is useful as a reagent in specific binding assays which employ nonradioisotopic labels. U.S. Pat. application Ser. No. 917,961, filed June 22, 1978 and assigned to the present assignee, describes such a binding assay employing an organic prosthetic group as the label. A preferred organic prosthetic group label is FAD which can be monitored during the course of the assay based on its ability to combine with a corresponding apoenzyme, preferably apoglucose oxidase, to form a catalytically active holoenzyme.

An illustrative FAD-labeled specific binding assay employing apoglucose oxidase as a monitoring reagent comprises an initial step of placing the ligand to be determined, usually an antigen or hapten, in competition with an FAD-labeled form of the ligand for binding to a limited quantity binding partner, e.g., an antibody, of the ligand. The level of ligand present determines the proportion of the FAD-labeled ligand resulting in the so-called "bound" species, consituting FAD-labeled ligand bound to the binding partner, and the "free" species, consituting FAD-labeled ligand not so bound. The amount of FAD activity resulting in either of the bound- or free-species is therefore a function of the amount of ligand in the test sample. In the usual circumstance, the bound-species form of the FAD-labeled ligand, in comparison to its free-species form, has significantly decreased FAD activity as measured by its ability to combine with apoglucose oxidase to form an enzymatically active conjugate. Thus, upon introduction of apoglucose oxidase to the system, the amount of resulting glucose oxidase activity is a function of the amount of ligand in the test sample and can be readily determined by known spectrophotometric techniques.

Apoglucose oxidase is not commercially available and has been the subject of only a few technical publications. The prior art method of choice for preparing apoglucose oxidase is described by Swoboda in Biochim. Biophys. Acta 175:365-379(1969). The object of Swoboda's study was the relationship between molecular conformation and the binding of FAD in glucose oxidase. Aware that FAD is relatively strongly bound to the apoenzyme and cannot be removed by dialysis at neutral pH, Swoboda developed a method for dissociating and separating FAD and the apoprotein based on treatment with acidified ammonium sulfate.

In the Swoboda method, glucose oxidase is added dropwise at $-5°$ C. to saturated aqueous ammonium sulfate solution acidified to pH 1.4 with sulfuric acid. About 80% of the FAD is dissociated from the apoenzyme before the protein precipitates. After removal of the supernatant by centrifugation, the precipitate is redissolved and neutralized in sodium acetate solution. The neutralized solution is recycled several times through the acidifed salt treatment, centrifugation, and neutralization steps. The apoenzyme is then precipitated with saturated ammonium sulfate solution and again redissolved in buffer. Residual solids, including denatured protein, are removed by centrifugation yielding an aqueous apoenzyme preparation.

While the Swoboda method produces apoglucose oxidase useful for certain research purposes, the preparations obtained have significant residual glucose oxidase activity due to incomplete dissociation and separation of FAD. Residual enzyme activities of typical Swoboda preparations, expressed as a percent of glucose oxidase activity of the apoenzyme preparation in the presence of excess FAD, fall in the range of 1–10%, with some investigators reporting apoenzyme preparations with residual activities as high as 20% or more [Zappelli et al, Eur. J. Biochem 89:491-499(1978)].

The apoenzyme preparations obtained following the method of Swoboda have sufficiently low residual activities to permit a demonstration of the operability of FAD-labeled specific binding assays employing the apoenzyme as a monitoring reagent, however, the residual activities are undesirable from a commercial standpoint. Additional difficulties with the Swoboda method which arise in developing a commercial assay are the variable residual activities found from preparation to preparation and the cumbersome nature of the cycling treatments required. Accordingly, it is the object of the present invention to provide an improved method for preparing apoglucose oxidase whereby residual enzyme activities several times less than those obtained by the prior art methods are consistently produced.

SUMMARY OF THE INVENTION

The present method for preparing apoglucose oxidase comprises the fundamental steps of (a) incubating an aqueous solution of glucose oxidase containing between about 20 and about 40 percent by volume glycerol and having a pH of less than about 2, (b) separating resulting dissociated FAD from apoenzyme in the incubated solution by conventional column chromatography methods in an aqueous environment containing between about 20 and about 40 percent by volume glycerol and at a pH of less than about 2, and (c) collecting the apoglucose oxidase effluent followed by adjustment of the pH thereof to between about 6.0 and about 7.5 and treatment to remove trace FAD. The apoglucose oxidase preparations obtained by the present method have residual glucose oxidase activities consistently less than 0.05%, and usually less than 0.005%. Such low levels of residual enzyme activity are generally insignificant relative to the accurate and reproducible performance of FAD-labeled specific binding assays.

DESCRIPTION OF THE PREFERRED EMBODIMENTS

Incubation of glucose oxidase in acidic glycerol solution results in dissociation of FAD and the apoenzyme in an environment stabilized against denaturation of the apoprotein. In the presence of glycerol, the period of incubation can be extended far past the times permitted in the prior art techniques. Accordingly, the efficiency of the acid induced dissociation of FAD from the apoenzyme is greatly enhanced. The level of glycerol in the incubation solution will usually be between about 20 and about 40 percent by volume. Significantly lower concentrations of glycerol provide decreased protection against denaturation of the apoprotein resulting in poor yields of apoenzyme, while significantly higher concentrations provide increasingly viscous solutions, creating processing difficulties in the later purification steps, particularly those involving column chromatography. Preferably, a glycerol concentration of about 30% by volume is used. Glycerol is ideally suited for use in the present method due to its miscibility with water and its relatively low molecular weight, which permits easy removal of glycerol from the apoenzyme preparation if desired. Functional equivalents of glycerol in the performance of the present invention will be evident to those skilled in the art.

Efficient dissociation of FAD from the apoenzyme will be obtained at pH levels less than about 2, with a pH of about 1.4 being preferred. Any acid which does not chemically alter the apoenzyme may be used to obtain the necessary acidic conditions, with sulfuric acid being particularly useful.

In contrast to the very short time of exposure to acid permitted by the prior art methods, incubation times of from anywhere around 30 minutes to many hours are possible following the present method. An incubation time of between about 1 and about 3 hours, preferably about 2 hours, will normally be used at temperatures ranging from about $-10°$ to about $10°$ C., preferably about $4°$ C. Such incubation times are not permitted in the absence of glycerol without the virtually complete denaturation of the apoprotein.

After the acid-glycerol incubation step, the resulting dissociated FAD is conveniently separated from the apoenzyme fraction by conventional column chromatographic techniques. Various types of chromatographic adsorbents will be evident to those skilled in the art for use in selectively adsorbing FAD. The differences in molecular weight and ionic character of FAD compared to the apoenzyme permit a wide variety of chromatographic techniques to be used, including molecular sieve gel chromatography, affinity chromatography, and ion exchange chromatography. In order to maintain dissociation of FAD and the apoenzyme while protecting the apoprotein from denaturation, the column chromatography step is performed in an aqueous environment containing between about 20 and about 40 percent by volume glycerol and at a pH of less than about 2. Such environment is usually obtained by passing the incubated solution from the initial acid/glycerol step through a chromatographic column which has previously been equilibrated with an appropriate acidic glycerol solution. It is preferred that the column chromatography step be performed in the shortest time practicable, usually in less than about 40 minutes and most preferably in less than 30 minutes. Such time periods can be obtained depending upon the amount of incubated solution to be processed by adjustments of flow rate and column dimensions. The more rapid the column chromatography step the better the yield and the lower the residual enzyme activities of the resulting apoenzyme preparation.

A particularly useful column chromatography technique involves the use of cross-linked dextran gel as the FAD adsorbent. The incubated solution is passed through a column of cross-linked dextran gel which is equilibrated with an aqueous solution containing between about 20 and about 40 percent by volume glycerol and having a pH of less than about 2. The effluent fractions containing protein are collected. If this apoenzyme preparation is to be used without further purification, the fractions are combined and as soon as practicable the pH adjusted to between about 6.0 and about 7.5, preferably about 7.0, at which pH the apoenzyme is relatively stable.

Further purification of the column effluent containing the apoenzyme is generally preferred and can follow a wide variety of conventional techniques including adsorption of FAD from solution or further chromatography of a column or other type. Another alternative is to adjust the pH to between about 6.0 and about 7.5, thereby allowing any residual FAD present to recombine with apoenzyme forming active glucose oxidase, and then separating the apoenzyme from formed glucose oxidase by standard techniques such as isoelectric focusing, ultracentrifugation, or chromatography. The yield of apoenzyme is only slightly decreased by this purification technique since the vast bulk of FAD (95% or more) is removed by the initial column chromatography step, particularly where cross-linked dextran gel is used, leaving only a very small amount of FAD to combine with apoenzyme and decrease the yield thereof.

A particularly preferred technique for further purifying the apoenzyme effluent from the initial column chromatography step involves adsorption of FAD from solution with adjustment of pH to between about 6.0 and about 7.5, preferably about 7.0. The physical form and chemical nature of the adsorbent may be selected from the many alternatives available to one skilled in the art. The use of a finely divided form of the adsorbent is particularly attractive since it permits rapid adsorption and easy separation by filtration or centrifugation. Coated charcoal has been found to be a very efficient FAD adsorbent. As is known in the art of using finely divided charcoal as an adsorbent for separating low molecular weight materials from proteins, the charcoal particles are first coated by such substances as albumin or dextran to prevent adsorption of the protein itself to the particles.

The present method may be used to prepare apoglucose oxidase from glucose oxidase of any source and has been found to be particularly applicable to glucose oxidase isolated from *Aspergillus niger*. Such enzyme is available commercially in a variety of forms. Liquid enzyme preparations are preferably dialyzed to remove low molecular weight materials before initiating the acid/glycerol incubation step.

The apoglucose oxidase preparations of the present invention are consistently obtained in better and more reproducible yields and have greatly reduced residual enzyme activities compared to the prior art preparations. Depending upon the particular purification steps taken, the apoenzyme preparation can be obtained in a liquid or solid form. In liquid form, the preparation will usually contain between about 20 and about 40 percent, preferably about 30 percent, by volume glycerol which carries through from the initial incubation step, and may also contain conventional diluents, buffers, and stabilizing agents. A dry form of the preparation can be obtained by precipitation with such known agents as ammonium sulfate and polyethylene glycol or by lyophilization after removal of the major portion of residual glycerol.

The present method will be illustrated, but is not intended to be limited, by the following example.

EXAMPLE

Purified glucose oxidase with low catalase activity obtained from the Research Products Division of Miles Laboratories, Inc., Elkhart, Ind. USA, was dialyzed twice for 12 hours each against 0.5% weight to volume (w:v) aqueous solution of mannitol (30 volumes each). An aliquot of the dialysate containing approximately 80–100 milligrams (mg) of the enzyme was combined with glycerol at 4° C. to give a glycerol concentration in the resulting solution of 30% by volume (approximately 20 ml total volume) and the solution adjusted to pH 1.4 by addition of concentrated sulfuric acid ($H_2SO_4$). The solution was incubated at 4° C. for 2 hours and then passed through a column of Sephadex G-50 (Pharmacia Fine Chemicals, Uppsala, Sweden) at 4° C., equilibrated with 30% by volume glycerol adjusted to pH 1.4 with concentrated $H_2SO_4$. The eluted protein peak was collected (27 ml containing 74% by weight of material added to the column) and 200 mg bovine serum albumin was dissolved in the pooled eluate. Charcoal (600 mg; RIA grade from Schwarz-Mann, Orangeburg, N.Y. USA) was then added and the mixture neutralized by addition of 4.0 ml of 0.4 M phosphate buffer (pH 8.0) and sufficient 2 N sodium hydroxide to adjust the pH to 7.0. The mixture was stirred for 60 minutes at 4° C. and filtered successively through 0.8 micron and 0.22 micron Millipore filters (Millipore Corp., Bedford, Mass. USA). Sodium azide (10% w:v) was added to give a final concentration in the mixture of 0.1%.

The apoenzyme preparations obtained consistently had residual glucose oxidase activities of less than 0.05%, and usually less than 0.005%, whereas the best preparations obtained following the aforementioned method of Swoboda had residual activities of 1–2% with some preparations having residual activities as high as 10–20%. The apoenzyme preparations of the present invention were found useful in the aforementioned FAD-labeled specific binding assays, producing background enzyme levels which could be considered insignificant for the purposes of the assays.

What is claimed is:

1. A method for preparing apoglucose oxidase comprising the steps of:
   (a) incubating an aqueous solution of glucose oxidase containing between about 20 and about 40 percent by volume glycerol and having a pH of less than about 2,
   (b) separating resulting dissociated flavin adenine dinucleotide from apoglucose oxidase in said incubated solution by column chromatography in an aqueous environment containing between about 20 and about 40 percent by volume glycerol and at a pH of less than about 2, and
   (c) collecting effluent containing apoglucose oxidase and adjusting the pH thereof to between about 6.0 and about 7.5.

2. The method of claim 1 wherein the percent by volume of glycerol in the aqueous solution referred to in step (a) is about 30%.

3. The method of claim 1 or 2 wherein the percent by volume of glycerol in the aqueous environment referred to in step (b) is about 30%.

4. The method of claim 1 wherein the pH of the aqueous solution referred to in step (a) is about 1.4.

5. The method of claim 1 wherein step (b) is accomplished by passing the incubated solution through a column of cross-linked dextran gel equilibrated with an aqueous solution containing between about 20 and about 40 percent by volume glycerol and having a pH of less than about 2, and collecting the effluent containing protein.

6. A method for preparing apoglucose oxidase comprising the steps of:
   (a) incubating an aqueous solution of glucose oxidase containing between about 20 and about 40 percent by volume glycerol and having a pH of less that about 2,
   (b) passing the incubated solution through a chromatography column equilibrated with an aqueous solution containing between about 20 and about 40 percent by volume glycerol and having a pH of less than about 2,
   (c) collecting the effluent fractions containing protein,
   (d) adding an adsorbent for flavin adenine dinucleotide to the combined protein-containing effluent fractions and adjusting the pH of the resulting aqueous mixture to between about 6.0 and about 7.5, and
   (e) separating the adsorbent from the aqueous mixture, leaving an apoglucose oxidase solution.

7. The method of claim 6 wherein the percent by volume of glycerol in the aqueous solutions referred to in steps (a) and (b) is about 30%.

8. The method of claim 6 wherein the pH of the aqueous solutions referred to in steps (a) and (b) is about 1.4.

9. The method of claim 6 wherein said aqueous glucose oxidase solution is incubated at between about −10 and about 10° C. and for between about 1 and about 3 hours.

10. The method of claim 9 wherein said incubation is carried out at about 4° C. for about 2 hours.

11. The method of claim 6 wherein said adsorbent added in step (d) is in a finely divided form and is separated in step (e) by filtration.

12. The method of claim 6 wherein said adsorbent is finely divided coated charcoal.

13. The method of claim 6 wherein the pH of the resulting solution in step (d) is adjusted to about 7.0.

14. The method of claim 6 wherein the glucose oxidase used has been dialyzed to remove low molecular weight materials.

15. An apoglucose oxidase preparation characterized by a residual glucose oxidase activity of less than 0.05%.

16. An apoglucose oxidase preparation characterized by a residual glucose oxidase activity of less than 0.005%.

17. The preparation of claim 15 or 16 in the form of an aqueous solution containing between about 20 and about 40 percent by volume glycerol.

18. The preparation of claim 17 wherein the percent by volume of glycerol in the aqueous solution is about 30%.

19. The preparation of claims 15 or 16 in a dry form.

20. The preparation of claim 19 in a lyophilized form.

21. The method of claim 6 wherein said chromatography column is a column of cross-linked dextran gel.

* * * * *